United States Patent [19]

Elmi

[11] 4,293,544

[45] Oct. 6, 1981

[54] FLUID AND SEMI-FLUID COMPOSITIONS INCLUDING BENZOATE ESTERS

[75] Inventor: Steele J. Elmi, Midland Park, N.J.

[73] Assignee: Finetex Incorporated, Elmwood Park, N.J.

[21] Appl. No.: 100,917

[22] Filed: Dec. 6, 1979

Related U.S. Application Data

[63] Continuation-in-part of Ser. No. 18,250, Mar. 7, 1979.

[51] Int. Cl.³ .................. A61K 7/44; A61K 7/42; A61K 7/15
[52] U.S. Cl. .................................. 424/60; 424/47; 424/59; 424/65; 424/70; 424/73; 424/168; 424/349; 424/358; 424/359; 424/365
[58] Field of Search ................ 424/365, 59, 60

[56] References Cited

U.S. PATENT DOCUMENTS

| | | | |
|---|---|---|---|
| 970,662 | 9/1910 | Sulzberger | 260/410.5 |
| 2,428,450 | 3/1942 | Eitelman | 260/410.9 |
| 3,506,704 | 4/1970 | Miller et al. | 260/476 |
| 3,929,986 | 12/1975 | Bouillon et al. | 424/68 |
| 3,984,535 | 10/1976 | Ghilardi et al. | 424/70 |
| 3,998,788 | 12/1976 | Rubino | 424/68 |
| 4,065,564 | 12/1977 | Miles, Jr. et al. | 424/68 |
| 4,073,880 | 2/1978 | Pader et al. | 424/68 |
| 4,083,956 | 4/1978 | Shelton | 424/68 |
| 4,107,192 | 8/1978 | Bailey et al. | 260/410.5 |
| 4,113,852 | 9/1978 | Kenkare et al. | 424/68 |

*Primary Examiner*—Dale R. Ore
*Attorney, Agent, or Firm*—Weingram & Klauber

[57] ABSTRACT

Fluid or semi-fluid compositions of matter are disclosed for functional application to the human body as toiletries, cosmetics, topical pharmaceuticals and the like. The said compositions include as a vehicle or carrier, the benzoic acid esters of a mixture of $C_{12}$, $C_{13}$, $C_{14}$, and $C_{15}$ linear primary alcohols together with a functionally effective quantity of a substance carried by the said vehicle, which substance is either dissolved or emulsified with the vehicle. The alcohol mixture may comprise by weight from about 13 to 31% of said $C_{12}$ alcohol, 28 to 44% of the $C_{13}$ alcohol, 17 to 40% of the $C_{14}$ alcohol, and 12 to 19% of the $C_{15}$ alcohol. The compositions of the invention, when applied to or spread upon the skin, produce a dry, non-greasy, lubricating and satiny feel.

6 Claims, No Drawings

FLUID AND SEMI-FLUID COMPOSITIONS INCLUDING BENZOATE ESTERS

BACKGROUND OF INVENTION

This application is a continuation-in-part of my copending application Ser. No. 18,250, filed Mar. 7, 1979, and entitled "Antiperspirant Compositions".

In my above-mentioned copending application, there has been disclosed improved fluid antiperspirant compositions, suitable for application by a pump spray, or as a pressurized aerosol or a roll-on. These compositions utilize as the liquid carrier therein, benzoic acid esters of a mixture of linear primary alcohols in the $C_9$ to $C_{15}$ carbon chain length.

Antiperspirant compositions thus utilizing the benzoate liquid carriers aforementioned, are found to have markedly superior characteristics in comparison to prior art antiperspirant compositions intended for similar uses. The aforementioned benzoates are, e.g. characterized, among other things, by strikingly low odor, which is a most desirable characteristic for the formulations mentioned. The absence of odor also pertains to the breakdown products of these esters, which products can result subsequent to use of same, e.g. by oxidation at the body surface. These resultant oxidation products are also thus innocuous and odor-free.

The aforementioned benzoate liquid carriers further, are found in the antiperspirant products mentioned to yield very superior properties as respects settling times of the agitated antiperspirant compositions, as well as more rapid onset of efficacy.

The said antiperspirant compositions further, are characterized by a marked absence of oily or greasy feel when such compositions are deposited upon the skin surface. This is an important characteristic for aesthetic reasons, i.e. for consumer acceptance of such products based upon such carriers.

SUMMARY OF INVENTION

Now in accordance with the present invention it has been found that use of certain of the aforementioned mixtures of benzoic acid esters in formulations of various further fluid or semi-fluid compositions, provides resultant compositions having unusual and unexpected improvements in the properties of same—when compared to prior art compositions of a generally similar type, but utilizing conventional organic vehicles.

Fluid or semi-fluid compositions in accordance with the present invention are either solutions or emulsions. They are functionally useful for application to the human body as toiletries, cosmetics, topical pharmaceuticals, and the like. The said compositions in their most general form, include as a vehicle or carrier, the benzoic acid esters of a mixture of $C_{12}$, $C_{13}$, $C_{14}$ and $C_{15}$ linear primary alcohols, together with a functionally effective substance carried by the said vehicle, the said substance being either dissolved in or emulsified with the said vehicle. The compositions of the invention, when applied to or spread upon the skin, produce a dry, non-greasy, lubricating and satiny feel.

The organic liquid compositions utilized as vehicles in the compositions comprise, as aforementioned, the benzoic acid esters of a mixture of $C_{12}$, $C_{13}$, $C_{14}$ and $C_{15}$ linear primary alcohols. These benzoates are the reaction products of benzoic acid with a mixture of the aforementioned linear primary alcohols. The alcohol mixture may generally comprise by weight from about 13 to 31% of said $C_{12}$ alcohol, 28 to 44% of said $C_{13}$ alcohol, 17 to 40% of said $C_{14}$ alcohol, and 12 to 19% of said $C_{15}$ alcohol. Preferably the alcohol mixture comprises by weight from about 23 to 31% of $C_{12}$ alcohol, 32 to 44% of said $C_{13}$ alcohol, 17 to 23% of siad $C_{14}$ alcohol, and 12 to 18% of said $C_{15}$ alcohol.

The alcohol precursors used in preparing these vehicles include primary alcohols having a proportion of branching at the 2-carbon position. One class of such alcohols are primary alcohols of formula ROH, where R is a primary alkyl group with from 12 to 15 carbon atoms, which is additionally represented by the formula:

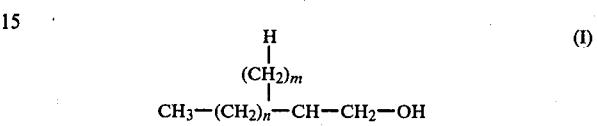

where m is a whole number from 0 to 6 inclusive, and n is a whole number from 6 to 12 inclusive such that $m+n=12$, 13, 14 or 15. In such alcohols at least 70% by weight of the alcohol of each specific chain length is linear (i.e. $m=0$) and the branching (if any) comprises about 50% of methyl groups with smaller amounts of ethyl, propyl, butyl, amyl and hexyl groups. These alcohols shall hereinafter be referred to in this specification by the term "linear primary alcohol", and are conveniently produced by the reaction of carbon monoxide and hydrogen with linear olefins having from 11 to 14 carbon atoms. The direct hydroformylation of olefins to give alcohols has been described, for example, in Kirk-Othmer, *Encyclopedia of Chemical Technology*, 3rd Ed., Vol. 1, p. 751, and references incorporated therein.

Blends of linear primary alcohols of the above type are manufactured by and commercially available from Shell Chemical Company, Houston, Texas, under the name NEODOL ®. These alcohols are also manufactured in the U.K. and Japan, using the same technology, and are marketed outside North America by Shell International Company, London, under the name DOBANOL.

DESCRIPTION OF PREFERRED EMBODIMENT

The invention will now be illustrated by a series of Examples, depicting compositions of various functional types such as toiletries, cosmetics, topical pharmaceuticals and the like. It will of course be understood, that the Examples now to be set forth are intended to be illustrative, and not delimitive of the invention. Compositions in accordance with the present invention, and which thus incorporate as a vehicle the aforementioned benzoate esters, are characterized by unexpected properties. The compositions of the invention markedly improve upon prior art compositions of generally similar type, which incorporate prior art organic vehicles—such as isopropyl myristate (IPM) or isopropyl palmitate (IPP). The benzoate esters utilized in the present composition are of extremely low toxicity. Further, the said benzoate esters are virtually odorless, in consequence of which there is no alteration in the desired odor characteristics of the composition e.g. if a toiletry or cosmetic, much less is there introduced an unpleasant odor such as can occur where prior art solvents are utilized, as for example IPM.

Of at least equal, if not greater importance for the present compositions, is the unexpected finding that the use therein of the aforementioned benzoate esters lends such compositions a non-greasy satiny feel when these compositions are applied and spread upon the skin. The consumer or user thus senses these compositions as providing a dry, lubricating, emollient feel—which is deemed very desirable for acceptance by such consumer. The said compositions further, function to prevent transepidermal loss of water, in consequence of which the skin remains moist and soft to the touch, despite the non-greasy aspects of the said compositions.

EXAMPLE I

Perfumes, colognes, or the like prepared in accordance with the present invention have outstanding attributes for the reasons aforementioned, i.e. the mixture of benzoate esters utilized as a vehicle imparts practically no odor of its own to the said perfume or cologne. In addition, the said compositions when applied to the skin produce a pleasant sensation, and induce conditioning of the skin. A representative perfume formulation was prepared, utilizing the following components in the indicated proportions:

| Component | % by wt. |
| --- | --- |
| Compounded fragrance oil | 10. |
| Benzoate esters* | 10. |
| S.D. (speciallydenatured) alcohol, anhydrous | approx. 79–80 |
| Color | q.s. |
| Antioxidant | |

*The benzoate esters utilized in this Example were the reaction products of benzoic acid with the NEODOL 25 product of Shell Chemical Co. NEODOL 25 is a mixture of $C_{12}$, $C_{13}$, $C_{14}$, and $C_{15}$ linear primary alcohols in weight percentages within the preferred ranges above set forth, i.e. 23 to 31% of the $C_{12}$ said alcohol, 32 to 44% of the $C_{13}$ said alcohol, 17 to 23% of the $C_{14}$ said alcohol, and 12 to 18% of the $C_{15}$ said alcohol. Thus, in a typical analysis of a NEODOL 25 sample, it was found to include by weight 29.4% of $C_{12}$, 36.7% of $C_{13}$, 18.3% of $C_{14}$, and 15.5% of the $C_{15}$ linear primary alcohol. In a typical preparation procedure a mixture of 227.7 parts (1.1 mol) of NEODOL 25, 122.0 parts (1.0 mol) of benzoic acid and 1.7 parts of methane sulfonic acid (as a catalyst) was stirred and heated under nitrogen to a temperature of 170° C. while collecting any distillate formed. When no more distillate came over and the acidity was less than 3 mg, it was cooled to 50° C. and washed with water and soda ash solution to a pH of 8–9. After washing again with a dilute salt solution, the ester layer was separated and heated under vacuum to remove traces of water. The benzoate product was a clear liquid with a surprisingly low odor.

In preparing the perfume of this Example the alcohol was combined with the antioxidant and mixed to dissolve. Thereupon the benzoate esters and fragrance oil are added and mixed. The resulting composition was chilled to 0° C., mixed, a filter aid added, and filtering carried out. As required color was added, mixed, and the final perfume composition was then ready for packaging. The resultant perfume composition was found to be a clear solution with the fragrance exhibiting its true character. The fixative nature of the vehicle was found to allow the fragrance to be sensed for a very extended period.

EXAMPLE II

In this Example, a satinized, protein bath oil was prepared in accordance with the present invention. More specifically, four sub-mixtures A, B, C, D were initially prepared which included individual components as follows:

| Component | | % by wt. |
| --- | --- | --- |
| A. | light mineral oil, N.F.** | 42.00 |
| | benzoate esters* | 23.00 |
| | lanolin oil** | 2.50 |
| | fragrances | 0.60 |
| | PEG-8 dilaurate** | 0.60 |
| | Lexein A440[1] | 5.00 |
| | PEG-4 dilaurate** | 3.60 |
| B. | benzoate esters* | 2.00 |
| | D & C Violet #2** | 0.0002 |
| | D & C Green #6** | 0.0001 |
| | antioxidant | 0.05 |
| C. | PEG-4 dilaurate** | 0.80 |
| | benzophenone-4** | 0.005 |
| D. | light mineral oil, N.F.** | 19.85 |

[1]myristyl hydrolyzed animal protein product of Inolex Corp., Chicago, Illinois 60609
*The benzoate esters utilized in this Example were in accordance with Example I.
**Identification is in accordance with CTFA Cosmetic Ingredient Dictionary, 2nd Ed., 1977. (Published by The Cosmetic Toiletry, and Fragrance Association, Inc., 1135 15th St., N.W., Washington, D.C. 20005.) Unless otherwise indicated, all name designations in the Examples of this specification shall have the same CTFA reference.

The procedure used in preparing the bath oil of this Example involved an initial combination of the components of sub-mixture A in the order listed therein. The combined components of sub-mixture B were mixed for five minutes and then added to sub-mixture A with additional mixing. The compounds of sub-mixture C were combined, mixed and dissolved, and then added to A and B, with further mixing for five minutes. Finally, the light mineral oil, i.e. sub-mixture D was added; and the total batch mixed for about 25 minutes. The resultant product is essentially an anhydrous solution in which the benzoate esters are a vehicle with the mineral oil. When applied to the skin, it was found to provide a very satiny feel. The moisture-laden protein is effectively locked to the skin by use of the said composition, to produce a soft, comfortable feeling at the skin surface. The product was found to yield a "dry hand", i.e. while acting as an excellent emollient, it nonetheless produced a smooth, non-oily feel upon the skin surface. This was especially surprising in view of the very high quantities of mineral and other oils present in the composition.

EXAMPLE III

In this Example a "suntan oil" in accordance with the invention was prepared. The following components were combined and mixed in the order listed:

| Component | % by wt. |
| --- | --- |
| benzoate esters* as vehicle | 85.8 |
| S.D. alcohol | 10.0 |
| octyl dimethyl PABA | 1.2 |
| lanolin oil | 2.5 |
| fragrance | 0.5 |

*As in Example I

The resultant composition was a non-greasy feeling, non-tacky oil with excellent spreading characteristics.

EXAMPLE IV

In this Example a "proteinized suntan oil" in accordance with the invention was prepared. The components of the composition were as follows:

| Component | % by weight |
| --- | --- |
| S.D. alcohol | 70.00 |
| benzoate esters* as vehicle | 20.00 |
| PEG-8 | 0.25 |
| hydroxypropyl cellulose | 0.75 |

| Component | % by weight |
| --- | --- |
| mink amido propyl dimethyl 2-hydroxyethyl ammonium chloride | 0.60 |
| hydrolyzed animal protein | 5.00 |
| octyl dimethyl PABA | 3.25 |
| fragrance | 0.15 |

*As in Example I

The alcohol was combined with the PEG-8 and mixed rapidly with addition of the hydroxyethyl cellulose. The resulant product was mixed for 45 minutes and the benzoate esters were than added. The remainder of the components were then added in the order listed, and further mixing was employed. The resultant final product was found to be water resistant and tack free on application. Although having a non-greasy feel, it yet displayed excellent emollient properties and prevented drying of the skin.

EXAMPLE V

In this Example a "sunscreen butter" in accordance with the invention was prepared. The following components were combined and mixed in the formulation:

| Component | % by wt. |
| --- | --- |
| benzoate esters* | 64.0 |
| $C_{12-15}$ alcohols*** | 18.5 |
| glyceryl $C_{18-36}$ wax acid ester | 8.0 |
| lanolin oil | 6.0 |
| lanolin alcohol | 1.0 |
| ethyl dihydroxypropyl PABA | 1.5 |
| steartrimonium hydrolyzed animal protein | 0.5 |
| fragrance | 0.5 |

*As in Example I
***NEODOL 25, described in Example I

The resultant composition was, again, a non-greasy feeling, dry, lubricating cream composition with excellent spreading characteristics.

Example VI

In this Example a cold cream cleanser in accordance with the invention was prepared. The components of the composition were as follows:

| Component | % by wt. |
| --- | --- |
| A. water | 53.60 |
| propylene glycol | 4.00 |
| magnesium aluminum stearate | 1.50 |
| B. glyceryl stearate, S.E. | 7.50 |
| mineral oil, light, N.F. | 14.80 |
| benzoate esters* as vehicle | 9.00 |
| lanolin oil | 0.50 |
| mineral oil (and) lanolin alcohol | 2.50 |
| cocyl sarcosine | 0.50 |
| methyl paraben | 0.10 |
| antioxidant | 0.50 |
| C. water | 1.00 |
| quaternium-15 | 0.10 |
| D. fragrance | 0.50 |

*As in Example I

In preparing the composition, the components of group A were mixed rapidly for 25 minutes and then heated to 70° C. The components of group B were then mixed and heated to 70° C. Group B was then added to group A while stirring. With continued stirring the mix was cooled to 40° C. The components of group C were mixed and added; further stirring was used, and the fragrance (D) was added. The composition was cooled to 25° C. to yield the final product.

The resultant product was an easily spreadable, effective cleansing cream. When applied to the skin, it left same soft and moisturized. Particularly to be noted was that the said product imparted a dry, non-oily lubricating feel—even (as here) in the presence of substantial quantities of mineral oil.

EXAMPLE VII

In this Example, a so-called "electric preshave" lotion was prepared in accordance with the invention. The composition included components as follows:

| Component | % by wt. |
| --- | --- |
| 1. S.D. alcohol | 85.8 |
| 2. cyclomethicone** | 10.0 |
| 3. benzoate esters* | 4.0 |
| 4. phenyl dimethicone | 0.1 |
| 5. fragrance | 0.1 |
| 6. color | q.s. |

*As in Example I
**CTFA designation for volatile silicone

In preparing the composition, components 2,3,4 and 5 were mixed and blended; component 6 is added, followed by thorough mixing; thereupon component 1 is added and further thorough mixing applied. The resulting product was a clear fluid which was easily and quickly applied to the face prior to shaving. It dried excess facial moisture and provided excellent lubrication to the face and electric shaver, to aid in providing a close, painless shave. Especially noteworthy was the dry, lubricated feel provided by the composition when applied to the skin. This is sharply contrasted with the oily feel which is present when a generally similar composition is used, which employs conventional IPM as a vehicle.

EXAMPLE VIII

In this Example an eye and throat oil was prepared in accordance with the invention. The composition included components as follows:

| Component | % by wt. |
| --- | --- |
| 1. benzoate esters* | 46.30 |
| 2. lanolin oil | 7.70 |
| 3. isopropyl lanolate & lanolin oil | 1.00 |
| 4. mineral oil, light, N.F. | 44.80 |
| 5. BHA | 0.05 |
| 6. propyl paraben | 0.05 |
| 7. fragrance | 0.10 |

*As in Example I

In preparing the composition, components 1 through 5 were combined and mixed. Component 6 was added and the blend mixed to dissolve. As necessary, the blend was warmed to 48°–50° C. Component 7 was added and the composition mixed for 15 minutes. The final resultant product was a quickly absorbed oil that left the skin with a velvet smooth film. The product had a dry, lubricating feel, even in the presence of very high amounts of mineral and other oils.

EXAMPLE IX

In this Example a "skin gel" was prepared in accordance with the invention. The composition included components as follows:

| Component | % by wt. |
|---|---|
| glyceryl tribehenate soap | 7.5 |
| benzoate esters* | 90.5 |
| fragrance, color, preservative | q.s. |

*As in Example I

In preparing the composition, the first two components were combined, mixed and heated to 110°–115° C. Mixing was continued and the blend cooled to 40°–45° C. The fragrance was added and mixed, and the blend cooled to 25°–27° C. to yield the final product. Such product was found to be a smooth, emollient, greaseless feeling skin gel, which was quickly absorbed by the skin, leaving a pleasant velvety afterfeel.

EXAMPLE X

In this Example a fingernail polish remover/conditioner was prepared in accordance with the invention. The composition included components as follows:

| Component | | % by wt. |
|---|---|---|
| A. | ethyl acetate | 15.00 |
| | acetone | 74.00 |
| | Abinco Gel "B"** | 1.00 |
| B. | protein fatty acid condensate | 1.10 |
| | acetylated lanolin alcohol | 1.00 |
| | benzoate esters* | 3.00 |
| | water | 4.00 |

**carbohydrate based mixed ester-ether gum product of Anheuser-Busch, Inc., St. Louis, MO
*As in Example I In preparing the composition, the ethylacetate and acetone were combined, the Abinco Gel "B" added, and the blend was mixed well for about 40 minutes, to swell the gum. While mixing, the components of group B were added in the order listed. The blend was thereupon mixed for 10 minutes to yield the final product. Such product, when utilized, prevented "whitening" and dryness of the fingers and skin, and provided dry lubrication and a good cosmetic feel and emolliency to the fingers.

EXAMPLE XI

In this Example a hair "brilliantine" was prepared in accordance with the invention. The composition included components as follows:

| Component | % by wt. |
|---|---|
| Acetulan** | 5.0 |
| benzoate esters* | 94.5 |
| fragrance | 0.5 |
| preservative, color | q.s. |

**acetylated lanolin alcohol product of Amerchol, Div. of CPC International, Edison, NJ 08817
*As in Example I In preparing the composition, the several components were combined and mixed in the order listed. The resultant product was a non-greasy, easily applied brilliantine, which increased hair gloss and provided a healthy appearance for same, while also making the hair manageable.

EXAMPLE XII

In this Example a hydrophilic ointment base was prepared—i.e. such ointment base was an oil-in-water emulsion. The base was typical of those used in topical pharmaceutical ointments and included components as follows:

| Component | | % by wt. |
|---|---|---|
| A. | stearyl alcohol | 5.00 |
| | cetyl alcohol | 5.00 |
| | glyceryl stearate, S.E. | 3.00 |
| | mineral oil | 3.00 |
| | benzoate esters* | 5.00 |
| | antioxidant | 0.10 |
| | Sorbitan Oleate | 2.00 |
| B. | water | 70.33 |
| | propylene glycol | 4.00 |
| | methyl paraben | 0.17 |
| | propyl paraben | 0.05 |
| | PEG-40 stearate | 0.75 |
| | Sta-Sol** | 0.85 |
| C. | Polysorbate 60 | 0.50 |
| | fragrance | 0.25 |

**lecithin product of A.E. Staley Mfg. Co., Decatur, Ill. 62525
*As in Example I In preparing the composition, the components of group A and the components of group B were separately mixed and heated to 65° C. With stirring, group A was then added to group B and mixed for 15 minutes. The blend was cooled to 35° C. and the group C components were added. The resultant product was a smooth spreading ointment base, which when applied to the skin provided a pleasant emolliency, yet without a greasy feel.

EXAMPLE XIII

In this Example a lipophilic ointment base was prepared—i.e. such ointment base was a water-in-oil emulsion. The base was again typical of those used in topical pharmaceutical ointments, and included components as follows:

| Component | | % by wt. |
|---|---|---|
| A. | benzoate esters* | 5.0 |
| | oleth-2 | 5.0 |
| | propyl paraben | 0.1 |
| B. | methyl paraben | 0.1 |
| | sorbitol | 5.0 |
| | water | 84.8 |

*As in Example I

In preparing the composition, the components of group A and the components of group B were separately combined and mixed. With stirring, group B was then slowly added to group A—with the stirring rate being increased as the emulsion thickened. The resultant product was again found to be a smooth spreading ointment base, which when applied to the skin provided a pleasant emolliency, without any greasy feel.

EXAMPLE XIV

In this Example a "personal deodorant" was prepared in accordance with the invention. The composition included components as follows:

| Component | % by wt. IN CONCENTRATE | % by wt. IN CAN |
|---|---|---|
| Triclosan+ | 0.15 | |
| benzoate esters* | 60.00 | |
| S.D. alcohol, 190 proof | 39.65 | 70.0 |
| fragrance | 0.20 | |

| Component | % by wt. IN CONCENTRATE | % by wt. IN CAN |
|---|---|---|
| propellant | — | 30.0 |

*As in Example I
+CTFA designation for Ciba-Geigy preservative

In preparing the composition, the Triclosan and benzoate esters were combined and mixed well. The alcohol and fragrance were added together and well mixed. The resulting concentrate was added to an aerosol container, and aerosol valve applied, and the container was pressurized with a suitable propellant. The product was tested, and was found to not only be an excellent deodorant, but when sprayed on the skin provided a dry emolliency, without any feeling of greasiness.

While the present invention has been set forth in terms of specific embodiments thereof, it will be understood in view of the present disclosure, that numerous variations are now enabled to those skilled in the art, which variations yet reside within the scope of the instant teaching. Accordingly, the invention is to be broadly construed, and limited only by the scope and spirit of the claims now appended hereto.

I claim:

1. In a sunscreening composition for application to the skin comprising a liquid vehicle together with an effective sunscreening amount of a sunscreening agent dissolved in the vehicle or emulsified along with the vehicle in the composition, the improvement comprising wherein the vehicle comprises the benzoic acid esters of a mixture of $C_{12}$, $C_{13}$, $C_{14}$ and $C_{15}$ linear primary alcohols, the alcohol mixture comprising by weight from about 23% to 31% of the $C_{12}$ alcohol, 32% to 44% of the $C_{13}$ alcohol, 17% to 23% of the $C_{14}$ alcohol, and 12% to 18% of the $C_{15}$ alcohol.

2. The sunscreening composition of claim 1, wherein the sunscreening agent is dissolved in the vehicle.

3. The sunscreening composition of claim 1, wherein the sunscreening agent is emulsified along with the vehicle in the composition.

4. The sunscreening composition of claim 1, wherein the sunscreening agent is a suntan oil.

5. The sunscreening composition of claim 1, wherein the sunscreening agent is octyl dimethyl PABA.

6. The sunscreening composition of claim 1, wherein the sunscreening agent is ethyl dihydroxypropyl PABA.

* * * * *